United States Patent [19]

Clay

[11] 4,047,849
[45] Sept. 13, 1977

[54] PNEUMATIC PULSATOR PUMPING SYSTEM WITH PULSATOR FLUID VENTING VALVE

[75] Inventor: Warren C. Clay, Lynn, Mass.
[73] Assignee: Thermo Electron Corporation, Waltham, Mass.
[21] Appl. No.: 647,680
[22] Filed: Jan. 9, 1976
[51] Int. Cl.² .......................... F04B 9/08; F04B 35/02
[52] U.S. Cl. .................................. 417/384; 417/388; 60/542; 137/102
[58] Field of Search ............... 417/385, 386, 387, 388, 417/478, 393; 60/542, 591, 533, 369, 467, 542; 91/280, 442; 137/102

[56] References Cited

U.S. PATENT DOCUMENTS

| | | | |
|---|---|---|---|
| 1,650,377 | 11/1927 | Nixon | 417/388 |
| 1,788,886 | 1/1931 | Nutt | 417/388 |
| 2,046,491 | 7/1936 | Scott | 417/478 |
| 3,200,831 | 8/1965 | Whitfield | 137/102 |
| 3,548,593 | 12/1970 | Valdespino | 60/542 |
| 3,551,076 | 12/1970 | Wilson | 417/385 |

*Primary Examiner*—Carlton R. Croyle
*Assistant Examiner*—Thomas I. Ross

*Attorney, Agent, or Firm*—James L. Neal; David W. Gomes

[57] ABSTRACT

A pneumatic pump adapted primarily as a left ventricular heart assist device includes a flexible bladder with a rigid housing. A pneumatic driver applies rhymical pulses between the bladder and the housing to repetitively collapse the bladder and establish a pumping action through the bladder, in conjunction with check valves in the inlet and outlet to the bladder. Between the driver and the pump there is provided a pneumatic pulse limiter which includes a flexible diaphragm isolating the driver from the pump. Pulses from the driver are transmitted to the pump only through the flexible diaphragm and the diaphragm is constrained to move only within established limits. Regardless of the magnitude of the pulse from the driver, the maximum pulse applied to the pump cannot exceed that corresponding to the maximum displacement of the diaphragm.

Between successive pulses, the portion of the system between the driver and the flexible diaphragm is depressurized. The rapidity with which depressurization occurs is enhanced by provision of a quick release valve between the driver and the diaphragm.

2 Claims, 4 Drawing Figures

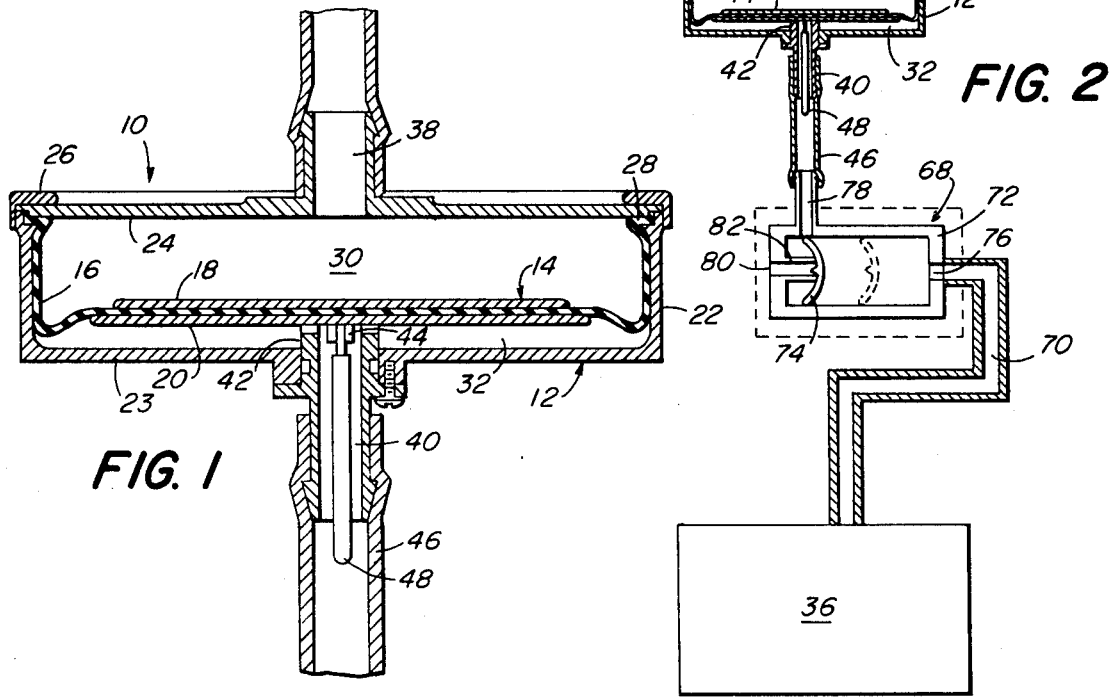

4,047,849

PNEUMATIC PULSATOR PUMPING SYSTEM WITH PULSATOR FLUID VENTING VALVE

The invention described herein was made in the course of or under a contract with the U.S. Department of Health, Education and Welfare.

BACKGROUND OF THE INVENTION

Efforts to develop artificial blood pumps have spanned approximately ten years, including research both in the area of heart assist devices and total heart replacement units. One prominent design involves a polyeurathane bladder enclosed in a rigid metal alloy housing. Pneumatic pulses applied between the bladder and the housing produce a pumping action through the bladder, in conjunction with check valves at the bladder inlet and outlet ports. Imposition of the pulse expels the contents of the bladder and termination of the pulse permits the bladder to refill. In a left ventricular assist device, the bladder inlet would be connected to the left ventrical. The ventricular pressure plus resiliancy in the bladder, if any, causes the bladder to refill. Thus the strength of the heart and the rate at which the pneumatic system is depressurized between successive pulses determine the rate at which the bladder is filled.

The inside surface of the bladder is flocked with fibers of a blood-compatible polymeric material which promote the formation of a stable biological layer along the surface of the bladder. To preserve this layer and to otherwise minimize blood damage, the inside surfaces of the bladder should not be permitted to contact each other during operation.

Accordingly, it is an object of this invention to provide a control device for controlling the collapse pattern of the flexible bladder in a pneumatic blood pump.

Another object of this invention is to promote rapid filling of the bladder during depressurization of the pneumatic system.

SUMMARY OF THE INVENTION

In a pneumatic pump of the type comprising a flexible bladder enclosed in a rigid housing, gas rhythmically injected and released between the bladder and the housing produces the desired pumping action in cooperation with one-way valves located at inlet and outlet ports to the pump. A fixed quantity of driving gas combined between the flexible bladder and the inner wall of the housing constitutes a pneumatic system which, when subjected to a pulse, transmits it to the bladder, expelling fluid therefrom. Between pulses the pneumatic system is depressurized. Compressed gas therein is promptly vented to minimize the time required for depressurization and, accordingly, promote rapid refilling of the bladder.

BRIEF DESCRIPTION OF THE DRAWINGS

FIG. 1 is a sectional view illustrating one embodiment of a pneumatic control device constructed in accordance with the present invention;

FIG. 2 illustrates the pneumatic control device of FIG. 1 installed in a pneumatically operated blood pump system;

FIG. 3 is a partially cut-away prospective view illustrating an alternate embodiment of a pneumatic control device constructed in accordance with the present invention.

DETAILED DESCRIPTION OF THE DRAWINGS

Figure 4:
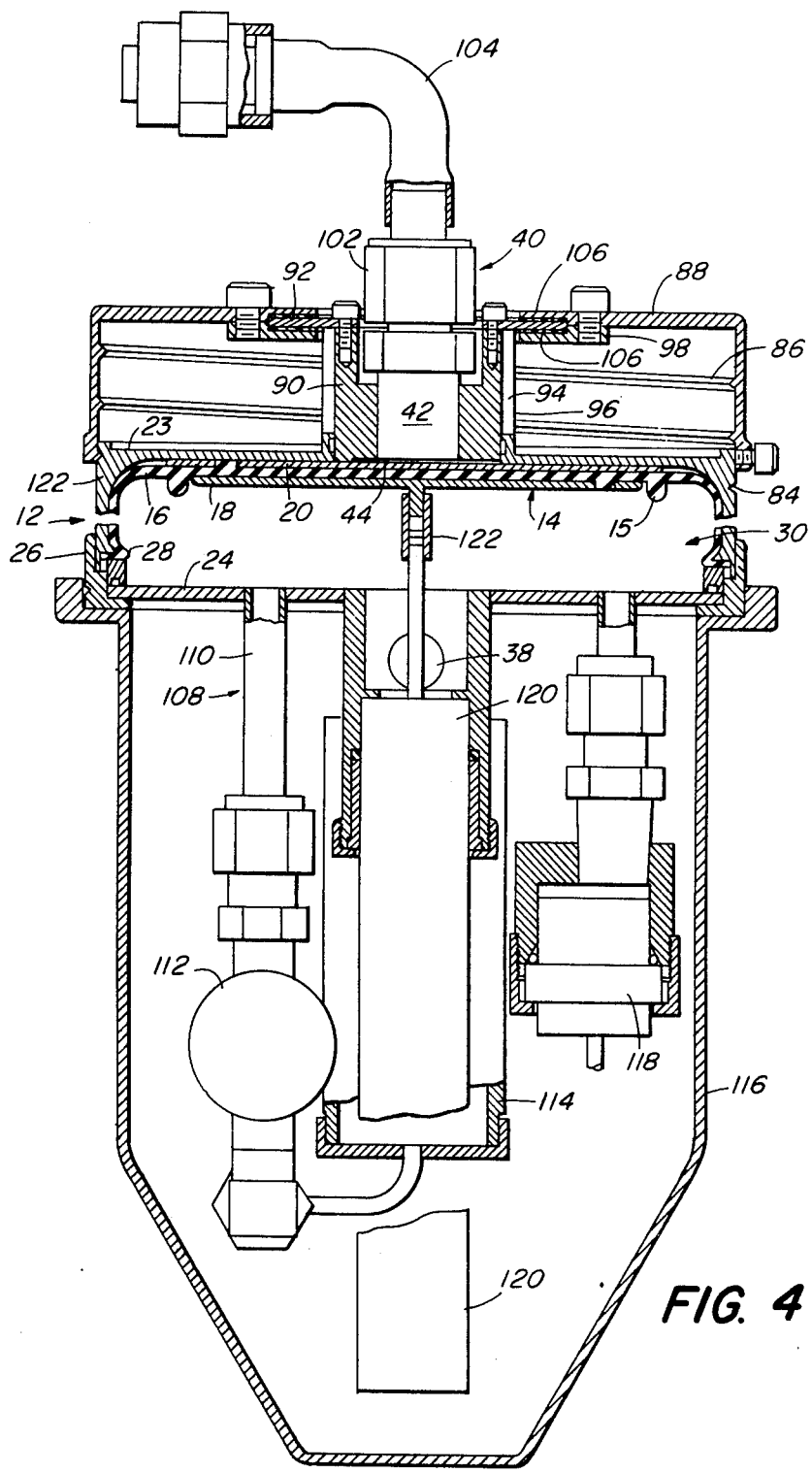
FIG. 4 is a sectional view of a pneumatic control device constructed in accordance with the present invention, including the structure represented in FIG. 3.

Referring to FIG. 1, there is disclosed a pneumatic control device 10 including a rigid cylindrical housing 12 confining therein a flexible diaphragm means 14. The diaphragm means 14 includes a flexible sealing member 16 having a shape complimentary to that of the housing 12 and adapted for rolling contact along the cylindrical walls of the housing. A central portion of the flexible sealing member 16 is provided with a pair of stiffeners 18 and 20 on opposite sides thereof. The housing 12 consists of an open cylinder 22 and closure 24 held together by an element 26. The peripheral edge 28 of the diaphragm means 14 is firmly held between the cylinder 22 and the closure 24. The housing 12 and the diaphragm means 14 thus define two chambers, 30 and 32, which are pneumatically isolated from each other by the flexible sealing member 16.

The pneumatic control device 10 is situated between pneumatically actuated pump means 34 and pneumatic driver means 36. From the chamber 30 there is provided a port 38 in pneumatic communication with a pump means 34, shown in FIG. 2. The pump means 34 may be more fully understood by reference to co-pending U.S. Pat. application Ser. No. 647,842, filed Jan. 9, 1976, for "Pneumatic Blood Pump" in the name of Victor L. Poirier. The chamber 32 is in pneumatic communication with the pneumatic driver means 36, shown in FIG. 2, through the means 40 forming a passageway. In the embodiment of FIG. 1, the passageway means 40 is centrally disposed in the cylinder 22 and an inward extension thereof forms a stop means 42 for engagement with the stiffener 20. The openings 44 are provided in the stop means 22 so that it does not block communication between the chamber 32 and the passageway means 40. The distance between the peripheral edge of the stop means 42 and the inner surface of the end wall 23 establishes the maximum volume of the chamber 30. As will hereafter be explained, the maximum volume of the chamber 30 determines the maximum stroke of the pump means 34, independently of the magnitude of pneumatic pulses supplied by the driver means 36.

Mounted upon the stiffener 20 and extending through the passageway means 40 into a transparent connecting tube 46 is an indicator 48. The indicator may be calibrated to indicate that position of the diaphragm means 14. When in the position of FIG. 1, it provides an indication of maximum stroke volume of the pump 34. During operation of the pump 34, the extent of its transilatory movement indicates whether or not the pump is operating on full stroke or partial stroke.

Reference is made to FIG. 2, where the pneumatic control device 10 is shown interposed betwen the pump means 34 and the pneumatic driver means 36. The pump means 34 includes a rigid housing 50 containing a flexible bladder 52 in communication with an inlet conduit 54 and an outlet conduit 56. At the locus of communication between the bladder 52 and the conduits 54 and 56 there appears, respectively, inlet valve means 58 and outlet valve means 60. The inlet valve means 58 and the outlet means 60 are both check valves which permit flow only in the direction of arrows 62. A port 64 in the housing 50 establishes fluid communication with the port 38 of the pneumatic control device, through the flexible tube 66. Fluid communication between chamber 32 and the pneumatic driver means 36 is established through the passageway means 40, the transparent connecting tube 46, a pneumatic release valve means 68 and a conduit 70.

The pneumatic release valve means 68 includes an elongated chamber 72 enclosing a reciprocal member 74. From one end of the chamber 72 a first port 76 communicates with the conduit 70. From a point in the sidewall of the conduit 70, adjacent the end opposite the first port 76, a second port 78 communicates with the tube 46. In the end of the elongated chamber 72 opposite the end forming the first port 76, there is formed a third port 80 in communication with the environment and associated with an inwardly extending tube 82. The pneumatic release valve means is constructed such that the reciprocal member 74 moves to the solid line position, as shown in FIG. 2, to block the port 80 and unblock the port 78. In this position fluid communication is established through the elongated chamber 72, between the pneumatic driver means 36 and the chamber 32 of the pneumatic control device 10. When the member 74 blocks the port 80, the reciprocating member 74 is positioned to locate a peripheral edge thereof immediately adjacent the inlet port 78 so that any flow from the chamber 32 and the tube 46 into the elongated chamber 72 will tend to dislodge the reciprocating member 74 from its blocking position and move it to its unblocking position, as represented by the broken line representation. A release valve which may be used in the presently described embodiment is a Humphrey Super Quick Exhaust Valve, available from Humphrey Products of Kalamazoo, Mich.

The pneumatic driver means 36 applies and releases pneumatic pulses in a rhythmical fashion. Upon generation of a positive pressure pulse above environmental pressure, the reciprocal member 74 advances to block a port 80 and establish communication between the pneumatic driver means 36 and the chamber 32. Imposition of the pulse in the chamber 32 advances the diaphragm means 14 from the stop means 42 to transmit the pulse to the pump means 34, between the bladder 52 and the housing 50. The pulse transmitted between the bladder and the housing is of a magnitude greater than arterial pressure present in the conduit 56 so that the bladder 52 will collapse and drive its contents into the conduit 56. Upon termination of the pulse from the driver means 36, pressure in the bladder 52 drops below arterial pressure in the conduit 56 and the valve means 60 snaps shut. The maximum stroke of the bladder (i.e. the maximum extent to which the bladder 52 can be collapsed) is determined by the volume of the chamber 30. When the diaphragm means 14 abuts the end of the housing 12 opposite the stop means 42, the bladder 52 cannot be further collapsed regardless of the force of the pulse emanating from the driver means 36.

At termination of the pulse, the pneumatic system which includes the chamber 32 is depressurized by the pneumatic driver means 36. Upon depressurization, initial flow from the chamber 32 to the elongated chamber 72 drives the reciprocal members 74 from the blocking position and opens the port 80 to the environment. Opening of the port 80 speeds depressurization of the pneumatic system which includes the chamber 32 and therefore minimizes the time required for refilling of the bladder 52, as will hereafter be further explained.

The elongated chamber 72 is situated in the pneumatic system so that, upon depressurization by the driver means 30, the compressed gas in the chamber 32 expands into the elongated chamber 72. The flow resulting therefrom is augmented by a similar expansion of air in the closed pneumatic system which incorporates the chamber 30 and also by venous pressure in conduit 54. The advantage of the pneumatic release valve means 68 is that it speeds depressurization and, as aforesaid, speeds refilling of the bladder 52. The pneumatic release valve 68 is situated closely adjacent to the pneumatic control device 10, thus permitting depressurization to occur close to the control device. When depressurization occurs only through the pneumatic driver means 36, the resistance inherent in the pneumatic system between the chamber 32 and the driver means 36 acts as a delay.

Reference is now made to FIG. 3 which discloses an alternate embodiment of the pneumatic control device of the present invention. The pneumatic control device of FIG. 3 is similar to that shown in FIG. 1 with the further provision that the stop means for limiting movement of the diaphragm means is adjustable. Like numerals are used to designate like parts.

The stop means 42, to establish limits upon movement of the diaphragm means 14, establishes the maximum volume of the chamber 30. Threads 84 are provided around the outer surface of the cylindrical housing 12 and mate with corresponding threads 86 of a hood 88. Associated with the hood 88, in a manner to be described hereafter, is a stop element 90 adapted to abut the stiffener 20. The passageway means 40 extends centrally through the stop element 90.

Along the upper periphery of the stop element 90 is attached a spider means 92, the arms of which extend through slots 94 in an extension 96 formed integrally with and extending outwardly from the end wall 23 of the cylinder 22. The extension 96 is configured to reciprocally constrain the stop element 90. The spider means 92 is affixed to the hood 88 by a plate 98 having a recessed area 100 adapted to accommodate the outwardly extended arms of the spider means 92. The plate 98 is affixed to the inner surface of the hood 88 so that the spider means links the hood 88 to the stop element 90. The surfaces of the hood 88 and the plate 98 which contact the outwardly extended arms of the spider means 92 may be lubricated, as by being coated with polytetrafluoroethylene or the like, to minimize friction.

Operation of the stop means 42 will now be described. Counterclockwise rotation of the hood 88 increases displacement of the hood from the end wall 23. Upon such rotation of the hood, the plate 98 rotates with respect to the spider means 92 and advances the spider means and the attached stop element 90 so that the periphery of the stop element adapted to engage the diaphragm means 14 approaches the end wall 23 of the cylinder 22. Maximum displacement occurs when the peripheral portion of the stop element 90 is coincident with the inner surface of the end wall 23. This condition defines the maximum volume for the chamber 30. Similarly, clockwise rotation of the hood 88 advances the stop element toward the closure 24 to reduce the maximum effective volume of the chamber 30. The stop element 90 having been positioned, the apparatus of FIG. 3 operates as that of FIG. 1. The annular bead 15 surrounding the stiffener 18 serves to avoid contact between the stiffener 18 and the closure 24 and to cushion the terminal portion of the stroke of the diaphragm means 14. It also insures precise cutoff of fluid flow through the port 38.

FIG. 4 is another view illustrating the apparatus of FIG. 3 in conjunction with certain associated equipment. Additionally, the stop means 42 is illustrated in the fully retracted position, establishing the maximum volume of the chamber 30. Like numerals are used to designate like parts.

The passageway means 40 extends through the stop element 90 and comprises a connection 102 adapted to receive a conduit 104 for establishing pneumatic communication with a pneumatic driver means. Teflon rings 106 are interposed between the spider means 92 and the hood 88 and between the spider means and the plate 98.

Communicating with the chamber 30 is vent means 108. The vent means comprises a line 110, solenoid valve in fluid communication with a container 114 holding a desiccant. The container 114 is open to the canister 116 and ultimately to the environment. In operation of the preferred embodiment herein described, the chamber 30 is at environmental pressure when in maximum volume state. To maintain this condition, the chamber 30 is periodically opened to the environment when the diaphragm means 14 is fully retracted against the stop means 42, whatever the position of the stop means. The solenoid valve 112 is opened to the environment. Air passing into the chamber 30 from the environment travels through the container 114 and is dehydrated by desiccant contained therein. Desiccant within container 114 may also serve to extract moisture from air within the chamber 30 which has collected there by diffusion through the wall of the bladder 52.

Also in communication with the chamber 30 is a pressure transducer 118 for providing a continuous signal proportional to pressure within the chamber. The output from the pressure transducer 118 may be used to provide an input to a monitoring device of the type described in co-pending U.S. Pat. application Ser. No. 647,841, filed Jan. 9, 1976, for "Pneumatic Pump Monitor" in the name of David Gernes (Docket No. 75-35). Further, in substitution of the indicator 48 illustrated in FIGS. 1 and 2, there may be provided a linear voltage displacement transducer 120 connected to the stiffener 20 through a means 122. The transducer 120 provides a voltage proportional to position of the diaphragm means, thereby providing an electrical signal analogous to the visual signal described in connection with the embodiment of FIGS. 1 and 2. As with the pressure transducer 118, the linear voltage transducer 120 is adapted to provide an input to a pump monitor as may be more fully understood by reference to the aforesaid co-pending U.S. Pat. application Ser. No. 647,841.

The present invention has been described with reference to various preferred embodiments. It should be understood, however, modifications may be made by those skilled in the art without departing from the scope of the invention.

I claim:
1. A blood circulatory assist device comprising:
   flexible bladder enclosed in a rigid housing and defining inlet means and outlet means for intermittently admitting and releasing blood to and from bladder;
   means forming a pneumatic system, including as a part thereof the space between said bladder and said housing;
   pneumatic pulse generator means for rhythmically pressurizing and pressure relieving said pneumatic system to rhythmically compress and release said flexible bladder;
   means dividing said pneumatic system interposed between said pneumatic generator and said circulatory assist device for transmitting pneumatic forces from one division of said pneumatic system to the other; and
   release valve means in said pneumatic system for venting said pneumatic system between said dividing means and said pneumatic generator in response to pressure relief by said pneumatic generator.

2. A blood circulatory assist device comprising:
   a flexible bladder enclosed in a rigid housing and defining inlet means and outlet means for intermittently admitting and releasing blood to and from said bladder;
   means forming a closed pneumatic system, including as a part thereof the space between said bladder and said housing, for transmitting pulses imparted thereto between said bladder and said housing;
   means forming a second pneumatic system pneumatically sealed from said closed pneumatic system, said second system being in physical communication with said closed system for transferring pneumatic pulses to said closed pneumatic system;
   pneumatic pulse generator means for rhythmically pressurizing and pressure relieving said second pneumatic system for transmitting rhythmical pneumatic pulses to said first pneumatic system and thereby rhythmically compressing and releasing said flexible bladder; and
   release valve means in said second pneumatic system proximate to said closed system for venting said second pneumatic system in response to pressure relief by said pneumatic generator.

* * * * *